US006545163B1

(12) United States Patent
Fruchey et al.

(10) Patent No.: US 6,545,163 B1
(45) Date of Patent: Apr. 8, 2003

(54) PROCESS TO PREPARE 1-ARYL-2-(1-IMIDAZOLYL) ALKYL ETHERS AND THIOETHERS

(75) Inventors: Olan Stanley Fruchey, Corpus Christi, TX (US); Brian David Burke, Portland, TX (US); Huh-Sun Chiou, Corpus Christi, TX (US); Michele L. Nichols, Friendswood, TX (US)

(73) Assignee: Napp Technologies, Saddle Brook, NJ (US)

( * ) Notice: Subject to any disclaimer, the term of this patent is extended or adjusted under 35 U.S.C. 154(b) by 1428 days.

(21) Appl. No.: 08/537,560

(22) Filed: Oct. 2, 1995

(51) Int. Cl.$^7$ .................. C07D 233/04; A61K 31/4164
(52) U.S. Cl. .............................. 548/315.1; 548/341.1; 548/346.1; 514/399; 514/400; 514/397; 504/139
(58) Field of Search .......................... 548/315.1, 341.1, 548/346.1; 514/399, 400, 397; 504/139

(56) References Cited

U.S. PATENT DOCUMENTS

| | | | | |
|---|---|---|---|---|
| 3,790,594 A | * | 2/1974 | Meiser et al. ............. | 548/315.1 |
| 3,839,574 A | * | 10/1974 | Godefrei et al. ...... | 548/315.1 X |
| 3,991,202 A | * | 11/1976 | Janssen et al. ....... | 548/315.1 X |
| 4,062,966 A | * | 12/1977 | Gymer ................ | 548/315.1 X |
| 4,107,314 A | * | 8/1978 | Cox et al. ............. | 548/315.1 X |
| 4,185,991 A | * | 1/1980 | Sasse et al. .......... | 548/315.1 X |
| 4,278,800 A | * | 7/1981 | Rentzea et al. ...... | 548/315.1 X |
| 4,590,203 A | * | 5/1986 | Binder et al. ................ | 514/397 |
| 4,636,514 A | * | 1/1987 | Rogers et al. ................ | 514/340 |
| 4,710,571 A | * | 12/1987 | Hofman et al. ............. | 544/216 |
| 4,749,717 A | * | 6/1988 | Kruse ......................... | 514/392 |
| 4,929,744 A | * | 5/1990 | Matthews et al. .......... | 548/202 |

FOREIGN PATENT DOCUMENTS

| | | | | |
|---|---|---|---|---|
| ES | 8506013 | 3/1984 | .............. | 548/315.1 |
| GB | 1522848 | 8/1978 | .............. | 548/315.1 |

OTHER PUBLICATIONS

C. L. Jackson, et al., "Researches on the Substituted Benzyl Compounds," *Am. Chem. Journ.*, 1:93 (1879/1880).

T. Thompson, et al., "Degradation of Quaternary Ammonium Salts, Part IV. Relative Migratory Velocities of Substituted Benzyl Radicals," *J. Chem. Comm.*, 55 (1932).

H.C. Urey, et al., "The Peroxide Effect in the Halogenation of Aromatic Side Chains," *J. Amer. Chem. Soc.*, 59(14):1405 (1937).

J. Bernstein, et al., "The Preparation and Properties of Some Substituted Benzyl Fluorides," *J. Amer. Chem. Soc.*, 70:2310 (1948).

E. Campaigne, et al., "3–Substituted Thiophenes. III. Antihistaminics of the N–(3–Thenyl)–Ethylenediamine Series," *J. Amer. Chem. Soc.*, 71:333 (1949).

G. S. Misra, et al., "Side–Chain Bromination of Some Aromatic Compounds With N–Bromosuccinimide," *Journal Indian Chem. Soc.*, 28(5):277 (1951).

R.G. W. Spickett, "The Synthesis of Compounds with Potential Anti–folic Acid Activity. Part I. 7–Amino–and 7–Hydroxy–pteridines," *J. Chem. Soc.*, 2887 (1954).

E. L. Eliel, et al., "Reactions of Esters with Tertiary Amines. II. The Reaction of Substituted Benzyldimethylamines," *J. Org. Chem.*, 19:1693 (1954).

T. N. Ghosh, et al., "On the Synthesis OF $\Delta^1$–Pyrroline Derivatives. Part I," *Journ. Indian Chem. Soc.*, 32(11):719 (1955).

M. J. Strauss, et al., "Intramolecular Nucleophilic Participation. VI. Forced Carbomethoxy Group Participation in the Solvolysis of 1–(2,6–Dicarbomethoxyphenyl)ethyl Bromide," *J. Amer. Chem. Soc*, 90(13):3473 (1968).

J. Jorge, et al., "Methanolysis (Solvolysis) and Synthesis of 4'–Substituted 4–Benzyloxy–benzyl Chlorides and Some Related Compounds: Comparisons with the Corresponding Benzoyl Compounds," *J. Chem. Soc. Perkin* Trans. II, 100 (1981).

M. Ouertani, et al., "The Easy Preparation of Many Benzlic Bromides Using Molecular Bromine as a Halogenating in the Presence of Catalytic Amounts of Lanthanum Tri–acetate," *Bull. Soc. Chim. Fr.*, 2(9–10):327 (1982).

R. Ashcroft, et al., "Homolytic Displacement at Carbon X*. Toluenesulphonyl Iodide as a Source of Toluenesulphonyl Radicals for the Formation of Allyl–Benzyl–, Cyclopropylcarbinyl–, Spirocyclopropylcycloalkyl–, Bicyclo[1.0.3] Alkyl–, and Bicyclo[1.0.4]Alkyl–4–Tolysulphones from Organocobaloximes" *Journalof Organometallic Chem.*, 289:403 (1985).

M. Raga, et al., "New Imidazole Antifungal Agents Derived From Benzo[b]Thiophene," *Eur. J. Med. Chem.—Chim. Ther.*, 21(4):329 (1986).

Yu, P. Volkov, et al., "Synthesis of 2–(3–Phenoxyphenyl) Isovaleric Acid and Its Esters Having Insecticidal Activity," *Bull. Sci. USSR Div. Chem. Sci.* (Engl. Transl), 35(6):1239 (1986).

L. Donxia, et al., "Kinetics and Linear Free Energy Relationship of Wittig Reaction Between Substituted enzaldehydes and Substituted Benzylidenetriphenylphosphorane", *Tetrahedron*, 42(15):4161 (1986).

(List continued on next page.)

*Primary Examiner*—Joseph K. McKane
*Assistant Examiner*—Golam M. M. Shameem
(74) *Attorney, Agent, or Firm*—Pennie & Edmonds LLP

(57) ABSTRACT

A process is disclosed for the preparation of imidazole derivatives, in particular, 1-aryl-2-(1-imidazolyl) alkyl ethers and thioethers, and more particular for the preparation of tioconazole. The preferred process involves alpha bromination of thiophene in cyclohexane, coupling with an imidazole to form the crude product, and forming the bisulfate salt thereof. The reaction utilizes less hazardous chemicals than currently employed for the production of 1-aryl-2-(1-imidazolyl) alkyl ethers and thioethers, and may be run at room temperature.

15 Claims, No Drawings

OTHER PUBLICATIONS

D. Tanner, et al., "Role of Cage Return and Solvent Viscosity in the Temperature–Dependent Kinetics of Benylic Bromination", *J. Org. Chem.*, 52:4686–4688 (1987).

A.S. Dneprovskii, et al., "Mechanisms of Free–Radical Reactions. XX. Reactivity in the Free–Radical Halogenation Reactions of Arylfluoroalkanes," *J. Org. Chem. USSR* (Engl. Transl.), 23(4):711 (1987).

11th Edition: "The Merck Index," Merck & Co., New Jersey entry 3476, p. 549; entry 6101, p. 972; and entry 9384, p. 1490 (1989).

Maier, "Organic Phosphorus Compounds 91.[1] Synthesis and Properties of 1–Amino–2–Arylethylphosphonic and–Phosphinic Acids as well as–Phosphine Oxides," *Phosphorus, Sulfur, and Silicon*, 53:43 (1990).

V. Truksa, et al., "Benzylic Hydrogen Atom Abstraction Utilizing Diethyl Bromomalonate as a Radical Source," *J. Org. Chem.*, 57:2967 (1992).

* cited by examiner

PROCESS TO PREPARE 1-ARYL-2-(1-IMIDAZOLYL) ALKYL ETHERS AND THIOETHERS

FIELD OF THE INVENTION

The invention relates to the preparation of imidazole derivatives and more particularly to the preparation of 1-aryl-2-(1-imidazolyl) alkyl ethers and thioethers.

BACKGROUND OF THE INVENTION

Imidazole derivatives, in particular, 1-[2-(2-chloro-3-thienyl)methoxy]-2-(2,4-dichlorophenyl)ethyl]-1H-imidazole, commonly referred to as tioconazole, are known for their antifungal therapeutic properties. U.S. Pat. No. 4,062,966 discloses a process for the preparation of 1-aryl-2-(1-imidazolyl) alkyl ethers and thioethers which employs arylation of an appropriate 1-aryl-2-(1-imidazolyl)alkanol or alkane thiol having the formula

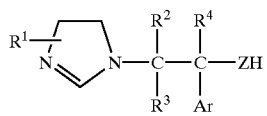

wherein $R^1$ to $R^4$ are each H or $C_{1-6}$ alkyl, Ar is phenyl, or substituted phenyl wherein said substitutents are halogen, $C_{1-6}$ alkyl, $C_{1-6}$ alkoxy, thienyl, or halothienyl, and, Z is oxygen or sulfur. In accordance with US '966, the reaction comprises converting the alcohol or thiol in a suitable solvent to its alkali metal derivative by treatment with a strong base, such as an alkali metal amide or hydride, and reacting with the appropriate aralkyl halide of the formula

where n is 1 or 2, Y is an aromatic heterocyclic group or substituted heterocyclic group, wherein substitutents are halogen, $C_{1-6}$ alkyl, or $C_{1-6}$ alkoxy atoms, thienyl or halothienyl group, and X is a halogen, preferably chlorine. Tetrahydrofuran (THF) is the preferred solvent taught in US '966. Reaction temperatures may range from about 0° C. to reflux temperature of the solvent and reaction times range from about 1 hour to about 24 hours. The product is isolated with water, extracted with ether, and may be purified as the free base or converted to a salt, e.g. the hydrochloride, and purified by recrystallization.

A disadvantage of the process disclosed in US '966 is that THF is a peroxide generator which presents the potential for an explosion. From a commercial viewpoint, peroxide generators are not preferred due to the dangers associated therewith.

GB 1 522 848 discloses a process for the preparation of imidazoles useful as antifungal agents involving a labor intensive, multi-sequence reaction of an imidazole ether with a reactive ester. Like US '966, THF is employed presenting similar concerns in the synthesis of the desired imidazole product.

According to the Pharmaceutical Manufacturing Encyclopedia, tioconazole is prepared by dissolving 1-(2,4-dichlorophenyl)-2-(1-imidazolyl)ethanol in THF and sodium hydride and heating to about 70° C. The resulting mixture is then contacted with 2-chloro-3-chloromethylthiophene and heated to reflux (about 67° C.). The resulting product is filtered, saturated with hydrogen chloride, triturated and recrystallized to obtain the purified tioconazole hydrochloride product having a melting point of about 170° C. This salt must then be freebased to form the product used in pharmaceutical formulations. This route, like those discussed above, also presents the dangers of a potential explosion.

There is thus a continuing need for a commercially viable, synthetic route for the production of imidazoles, in particular tioconazole.

SUMMARY OF THE INVENTION

The present invention relates broadly to a novel process for the preparation of 1-aryl-2-(1-imidazolyl) alkyl ethers and thioethers comprising (a) alpha bromination of an aromatic or a heterocyclic compound, or more particularly a thiophene derivative under suitable reaction conditions; and, (b) coupling under suitable reaction conditions the product of step (a) with an imidazole, preferably an imidazolyl ethanol derivative.

For exemplary purposes, the present invention is described in particular detail with respect to the preparation of tioconazole. It is to be understood that the process is applicable to other aromatic or heterocyclic compounds, e.g. econazole or miconazole.

Relative to the preparation of tioconazole, it is preferred that the product of step (b) be converted to a bisulfate salt for ease of isolation and purification of the final product. Reaction conditions for step (a) include free radical alpha bromination, preferably employing n-bromosuccinimide (NBS) in a refluxing aliphatic solvent such as cyclohexane. Reaction conditions for step (b) include a temperature range of about 15° C. to about 30° C., use of an alcohol or short chain (e.g., $C_{5-10}$) aliphatic hydrocarbon as solvent, and employing a reaction time of from about 1 to about 24 hours.

DETAILED DESCRIPTION OF THE INVENTION

The present invention relates broadly to a process for the preparation of 1-aryl-2-(1-imidazolyl) alkyl ethers and thioethers comprising
  (a) alpha brominating an aromatic or heterocyclic compound, preferably a thiophene derivative under suitable reaction conditions; and,
  (b) coupling the product of step (a) with an imidazole, preferably an imidazolyl ethanol derivative under suitable reaction conditions. Purification of the product of step (b) is preferably accomplished as the bisulfate salt.

More specifically, the present invention relates to a process for the preparation of tioconazole comprising (a) alpha bromination of 2-chloro-3-methylthiophene, using NBS in the presence of a peroxide and aliphatic solvent under suitable reaction conditions; and, (b) contacting the product solution of step (a) with 1-(2,4-dichlorphenyl)-2-(1-imidazolyl)ethanol under suitable reaction conditions.

The reaction will be described below relative to each reaction step.

Step A

Alpha Bromination:

One embodiment of the present invention involves, as step (a), alpha bromination with a brominating agent in the presence of an aliphatic solvent and a free radical initiator. Any suitable brominating agent may be employed. Suitable brominating agents include but are not limited to NBS, molecular bromine, 1,3-dibromo-5,5-dimethyl hydantoin, n-bromoacetamide. N-bromosuccinimide is the preferred brominating agent.

The process may be employed to brominate the alkyl side chain of alkyl-substituted heterocyclic or aromatic compounds. The alkyl side chain can have from 1 to about 4 carbon atoms and is preferably a saturated hydrocarbyl radical. Typical of such alkyl side chains include methyl, ethyl, propyl and butyl radicals. Preferably, the alkyl radical is a methyl radical.

Typical of the aryl or heterocyclic compounds with which the brominated intermediate (produced by the process of step (a)) can be employed include toluene, thiophene, furan, pyridine, 2-methylpyridine, lutidine, methylquinoline, dimethylfuran and similar heterocyclic compounds. Thiophene compounds are of particular interest. Most preferred are 2- and 3-methyl thiophene and most particularly preferred is 3-methyl thiophene.

The molar ratio of brominating agent to aryl or heterocyclic is preferably 1:1. However, an excess of starting heterocyclic material above stoichiometric can be employed.

The alpha bromination is preferably carried out in a solvent that facilitates the alpha bromination. Prior art studies have shown that certain brominators take place with more facility in one solvent versus another solvent. It has been found that aliphatic solvents, such as hexane, and in particular cycloaliphatic solvents such as cyclohexane show good selectivity. It has also been found that satisfactory selectivity and yield can be obtained by carrying out the process of step (a) with an initial concentration of heterocyclic of about 5 to about 20 percent (%) by weight (wt) in the solvent.

The time of the reaction is only that necessary to complete the reaction and the reaction can generally be carried out at elevated temperature (e.g., refluxing cyclohexane) under atmospheric conditions. Generally, reaction times for step (a) comprise about 1 hour to about 12 hours. More generally the reaction is performed in about 4 hours.

In general, suitable organic peroxides may be employed as free radical initiators. Suitable initiators include but are not limited to peracetic acid, perbenzoic acid, perbutyric acid, toluenesulfonic acid, benzoyl peroxide, azobisisobutyronitrile, and the like, with benzoyl peroxide being the preferred initiator. Generally a catalytic amount of peroxide is employed to achieve complete conversion. The weight ratio of peroxide to thiophene is about 0.01 to about 0.30, in particular about 0.01 to about 0.10, and most preferred about 0.02 to about 0.08.

In one embodiment of the present invention, 2-chloro-3-methylthiophene is brominated with NBS and benzoyl peroxide as a radical initiator. We have discovered good selectivity to the alpha brominated material (results in about 75% yield ) with this reaction step. Reaction proceeds through this brominated site.

A significant point of this particular reaction is that this is a Wohl-Zeigler reaction which is generally run in carbon tetrachloride solvent. With carbon tetrachloride one must usually isolate the intermediate since the solvent can then react further with the product of the coupling step. We have discovered that cyclohexane may be employed as a solvent with this Wohl-Zeigler reaction. Once the desired brominated product is formed, one may easily filter off the solid succinimide byproduct formed. It is recommended as the easiest, and most safe route, to not isolate the brominated thiophene product of step (a), but take the crude solution and proceed to the subsequent coupling reaction.

Step B

Coupling:

The solution product of step (a) is coupled with an imidazolyl derivative with a base and alcohol as solvent. A preferred imidazolyl derivative is 1-(2,4-dichlorophenyl)-2-(1-imidazolyl)ethanol, but others may be employed. The cyclohexane solution product of step (a) is poured into an imidazolyl, hydroxide, alcohol reaction mixture. At this point, a mixed solvent system of cyclohexane and alcohol is present. The coupling reaction is conducted at room temperature, generally run overnight, and results in the desired tioconazole product with sodium bromide as a byproduct. Yields of about 40% of the crude tioconazole based on product of step (a), (i.e., thiophenol converted to brominated intermediate) have been obtained.

Suitable reaction conditions for step (b) comprise a temperature range of about 15° C. to about 30° C., preferably about 20–25° C., most preferably at about room temperature. It was discovered that conducting the reaction at a temperature less than reflux of the solvent results in higher yields, and decreases decomposition of the 2-chloro-2 bromomethylthiophen starting material (which is a severe lacryamator). Additionally, a reaction temperature as close to room temperature as possible minimizes formation of byproducts.

Suitable solvents for the reaction comprise alcohols such as methanol, ethanol, isopropanol, and the like. The reaction is preferably conducted in isopropanol as solvent. Alternate solvents include, but are not limited to short chain alcohols (e.g., $C_{1-6}$) provided reagents are soluble at room temperature therein. It is preferred to avoid solvents which form peroxides. It was discovered that the coupling product has limited solubility in solvents such as alkanes, aromatics, hexane, heptane, toluene, benzene.

Reaction times for step (b) comprise about 1 to about 24 hours, preferably about 12 hours.

Suitable bases include sodium hydroxide (NaOH), sodium hydride (NaH), potassium hydroxide, sodium isopropoxide and the like. The preferred base to employ is sodium hydroxide.

We have discovered that replacing NaOH for NaH which is normally employed by the art, and using isopropanol as solvent instead of THF eliminates the hazards of a peroxide former, and hence the danger of explosion associated therewith, as well as the evolution of hydrogen gas. When one employs NaH, all reagents go to their respective salts; with NaOH as a base, there is an equilibrium in the reaction. As the reaction proceeds the equilibrium is shifted towards the product and less impurities are formed.

Step C

Purify/Conversion to Salt

In accordance with the present invention , the product of step (b) is converted to its corresponding bisulfate salt (not chloride salt as described in the art). To the crude tioconazole formed from step (b) a solvent switch is performed. Water is added to the reaction mixture of step (b) and the isopropanol/cyclohexanol solvent is removed, preferably by distillation. The desired product remains in the pot as an water/oil mixture. Solvent, such as xylene, is added to the water/oil mixture to form 2 mobile phases and the phases are separated. To the organic phase is added sulfuric acid to form the bisulfate salt. Addition of acetone causes formation of white crystals. The white crystals are filtered and recrystallized in an aqueous medium, preferably water. The tioconazole bisulfate salt has a melting point of about 80° C.

Relative to the art, the present invention has now eliminated the need for hazardous solvents, use of hydrogen formers, the need to run reactions at elevated or reflux temperatures, and provides a process which allows water as a recrystallization solvent. The tioconazole bisulfate salt has been found to be more readily crystallized than the corresponding chloride salt in water.

To liberate the tioconazole free base, the bisulfate salt is added to a cyclohexane/water mixture and heated. A neutralizing base, preferably ammonium hydroxide is added to the warm solution and phases separated. Base is added in an amount sufficient to neutralize the bisulfate salt. As the cyclohexane solution cools tioconazole crystallizes out of solution. It was truly an accidental discovery to find that the tioconazole is soluble in cyclohexane.

Color Treatment:

As an optional measure, to remove some color bodies formed, aluminum oxide (alumina), alone or in combination with other decolorizing agents is employed. The art generally employs activated carbon to remove color bodies. It was found that alumina in conjunction with activated carbon when added to the liberated tioconazole heated in a suitable solvent, preferably a cycloaliphatic solvent, most preferably cyclohexane, results in a whiter tioconazole product.

For exemplary purposes, the present invention was described in particular detail with respect to the preparation of tioconazole. For preparation of compounds such as econazole or miconazole wherein a similar procedure may be employed, the starting aromatic compounds include dichloro toluene and chloro toluene respectively. Like tioconazole, 1-(2,4-dichlorophenyl)-2-(1-imidazolyl) ethanol may be employed as the imidazolyl compound for the coupling step.

EXAMPLES

The following examples are intended to illustrate one embodiment of the present invention and are not intended to limit the scope or utility thereof.

Example 1

NaOH, Bisulfate Color Treatment (@0.4 Mole Scale)

(Step A): A reactor was charged with 2-chloro-3-methylthiophene (about 53.0 g), cyclohexane (about 183.4 g) and benzoyl peroxide (about 1.0 g) and the mixture heated to reflux with stirring. N-bromosuccinimide (about 78.0 g) and benzoyl peroxide (about 4.0 g) were placed in a separate beaker and mixed well. While refluxing, the thiophene solid mixture was charged to the NBS reactor in small portions over approximately a one hour period and stirring and refluxing continued for about an additional two hour period. The resultant solution was cooled to room temperature, and the solids removed from the solution via filtration and rinsed with cyclohexane. The mother/wash liquor (a cyclohexane solution of 2-chloro-3-bromomethylthiophene) is saved for further processing.

(Step B) A second reactor was charged with about 1-(2, 4-dichlorophenyl)-2-(1-imidazolyl)ethanol (about 102.9 g), sodium hydroxide pellets (about 15.7 g) and isopropanol (about 384.1 g). The contents were stirred and refluxed for about three hours. After cooling to room temperature, the cyclohexane solution of 2-chloro-3-bromomethylthiophene of step A was added to the reactor and the contents stirred overnight yielding a solution of crude tioconazole and solid sodium bromide. Water (about 75.7 g) was added to the reaction mixture to dissolve the solids. The crude reaction yield was ca. 49% based on 2-chloro-3-methylthiophene.

(Step C) Xylene (about 250 ml) was charged to the crude reaction mixture. Water was added to dissolve the solid sodium bromide byproduct. The two phase mixture was separated. The aqueous phase (lower) was removed and sulfuric acid (about 22.5 ml) was added to the reactor forming the bisulfate salt of tioconazole. The contents were slowly cooled to about 65° C. The heat was removed and acetone (about 200 ml) was slowly added to cool and crystallize tio-bisulfate, yielding off-white crystals which were filtered when the temperature reached about 10° C. The solids were then washed with cold acetone. (Water Recrystallization) Activated carbon (about 0.82 g) was charged with water (about 160 ml) and tioconazole salt solids in a small round bottom flask and heated to reflux for about 2 hours. The hot solution was filtered through a celite bed. Upon cooling, white solids evolved and were filtered, washed with cold water, and dried overnight.

(Liberating Free Base) The tioconazole salt solids were combined with water (about 100 ml) and cyclohexane (about 210 ml) in a reactor to form a three phase system. While stirring, about 29% ammonium hydroxide (about 16.8 g) was charged, ensuring a pH of about 10 in the aqueous phase. The free base was dissolved into the cyclohexane at about 60° C. The aqueous phase (lower) was removed and the cyclohexane solution cooled slowly. A seed tioconazole (about 0.1 g) was charged to the reactor when the temperature reached about 40° C. Cooling continued. The resultant white solids were filtered and washed with cyclohexane (about 75 ml). Upon drying (solids @47.9 g) at about 50° C. under vacuum, a yield of ca. 30.9% based on 2-chloro-3-methylthiophene was realized.

Example 2

NaOH, Freebase Color Treatment (@0.4 Mole Scale)

Step A of example 1 was repeated.

Step B of example 1 was repeated with the exception of employing about 87 g of 1-(2,4-dichlorophenyl)-2-(1-imidazolyl)ethanol.

Step C of example 1 was repeated with the exception of reversing the order of water and xylene addition. Purification proceeded as described except no color treatment was performed at the water recrystallization step. The liberating free base step was performed as per example 1 except that cyclohexane solution was color treated for about 2 hours with about 2.4 g carbon and about 2.4 g alumina before final crystallization. After cooling to room temperature, crystallization occurred without seeding. The white solids (about 37.9 g) were filtered and dried (about 37.4 g) at about 50° C. under vacuum, to obtain a yield of ca. 24.2% based on 2-chloro-3-methylthiophene.

Example 3

TYPE—NaH @ Room Temperature (@0.4 Mole Scale)

Step A of example 1 was repeated with the exception that a larger scale (0.8 mole) was used to synthesize the 2-chloro-3-bromomethyl thiophene. The final filtrate of this step was divided into 2 equal portions, so only 0.4 mole scale went forward.

A second reactor was charged with NaH (about 16.0 g) and cyclohexane (about 193.8 g) and stirred. Isopropanol (about 157.7 g) was charged to an addition funnel and slowly added to the reactor as $H_2$ evolved. The mixture was heated to reflux for about 1 hour. 1-(2,4-dichlorophenyl)-2-(1-imidazolyl)ethanol (about 102.8 g) and isopropanol (about 286.6 g) were charged to an Erlynmeyer and heated with stirring until all solids dissolved. The hot solution was then transferred to the refluxing reactor and the resulting solution continued to reflux for about 2.5 hours. After cooling to room temperature, the cyclohexane solution of 2-chloro-3-bromomethylthiophene was added to the reactor containing the imidazolyl mixture and the contents were stirred at room temperature overnight yielding a solution of crude tioconazole and solid sodium bromide. Water (about 37.1 g) was charged to the reactor. The crude reaction yield was ca. 44.6% based on 2-chloro-3-methylthiophene.

Example 4

NaH @ Reflux (@0.2 Mole Scale)

Step A of example 1 was repeated with the following exceptions: 2-chloro-3-methylthiophene (about 26.6 g), cyclohexane (about 93.6 g) and benzoyl peroxide (about 1.0 g),. N-bromosuccinimide (about 36.5 g) and benzoyl peroxide (about 3.1 g) were employed.

Step B of example 3 was repeated with the following exceptions: NaH (about 6.4 g), cyclohexane (about 75.6 g), 1-(2,4-dichlorophenyl)-2-(1-imidazolyl)ethanol (about 41.2 g), and isopropanol (228 g) were employed. The cyclohexane solution of 2-chloro-3-bromomethylthiophene was then added to the reactor containing the imidazolyl mixture and the contents stirred at reflux for 4 hours, yielding a solution of crude tioconazole and solid sodium bromide. Processing continued in accordance with example 3. The crude reaction yield is ca. 25.3% based on 2-chloro-3-methylthiophene.

Example 5

THF @ Room Temperature (@0.2 Mole Scale)

Step A of example 1 was repeated with the following exceptions: 2-chloro-3-methylthiophene (about 26.7 g), cyclohexane (about 91.3 g), benzoyl peroxide (about 1.0 g), N-bromosuccinimide (about 35.7 g) were employed.

Step B: A second reactor was charged with 1-(2,4-dichlorophenyl)-2-(1-imidazolyl)ethanol (about 43.7 g) and tetrahydrofuran (THF)(about 263.9 g). The mixture was heated with stirring to about 30° C. and then cooled to about 25° C. NaH (about 6.4 g) was charged slowly to the reactor as $H_2$ evolved. The mixture was heated to reflux for about 2 hours. The solution was cooled to room temperature and many solids crystallized out of solution. The cyclohexane solution of 2-chloro-3-bromomethylthiophene was then added to the reactor containing imidazoyl and the contents were stirred overnight, yielding a solution of crude tioconazole and solid sodium bromide. The crude reaction yield is ca. 37.9% based on 2-chloro-3-methylthiophene.

What is claimed is:

1. A process for the preparation of tioconazole comprising
   (a) alpha brominating 2-chloro-3-methylthiophene in the presence of a peroxide and cyclohexane solvent, under suitable reaction conditions; and,
   (b) contacting the product of step (a) with 1-(2,4-dichlorphenyl)-2-(1-imidazolyl)ethanol under suitable reaction conditions.

2. The process of claim 1 further comprising contacting the product of step(b) with sulfuric acid under suitable conditions to form a bisulfate salt.

3. The process of claim 2 wherein the bisulfate salt is isolated and recrystallized in an aqueous medium.

4. The process of claim 3 wherein the aqueous medium is water.

5. The process of claim 3 further comprising dissolving the bisulfate salt in a cyclo aliphatic solvent mixture and adding a base in a sufficient amount to liberate the salt therefrom.

6. The process of claim 3 wherein the base is ammonium hydroxide.

7. The process of claim 6 wherein the product thereof is heated in a suitable solvent and a decolorizing agent is added thereto.

8. The process of claim 7 wherein the decolorizing agent is selected from the group consisting of alumina, activated carbon, or a combination thereof.

9. The process of claim 8 wherein the solvent is cyclohexane.

10. The process of claim 1 herein suitable reaction conditions for step (b) comprise a temperature range of about 15° C. to about 30° C.

11. The process of claim 1 wherein suitable reaction conditions for step (b) comprise $C_{1-6}$ alcohol as solvent.

12. The process of claim 1 wherein suitable reaction conditions for step (b) comprise a reaction time of about 1 to about 24 hours.

13. The process of claim 1 further comprising converting the product of step (b) to a bisulfate salt under suitable reaction conditions.

14. Tioconazole produced by the process of claim 1.

15. Tioconazole bisulfate salt.

* * * * *